(12) United States Patent
Ishida et al.

(10) Patent No.: US 8,524,056 B2
(45) Date of Patent: Sep. 3, 2013

(54) ELECTROCHEMICAL CORROSION POTENTIAL SENSOR

(75) Inventors: Kazushige Ishida, Hitachi (JP); Yoichi Wada, Hitachinaka (JP); Masahiko Tachibana, Hitachi (JP); Motomasa Fuse, Hitachinaka (JP); Naoshi Usui, Tsukuba (JP); Motohiro Aizawa, Hitachi (JP); Nobuyuki Ota, Hitachi (JP)

(73) Assignee: Hitachi-GE Nuclear Energy, Ltd., Ibaraki (JP)

( * ) Notice: Subject to any disclaimer, the term of this patent is extended or adjusted under 35 U.S.C. 154(b) by 693 days.

(21) Appl. No.: 12/696,355

(22) Filed: Jan. 29, 2010

(65) Prior Publication Data
US 2010/0206729 A1    Aug. 19, 2010

(30) Foreign Application Priority Data
Jan. 30, 2009    (JP) .................................. 2009-018947

(51) Int. Cl.
  *G01N 17/00*    (2006.01)
  *G01N 27/26*    (2006.01)
  *G21C 9/00*    (2006.01)

(52) U.S. Cl.
  USPC ......... 204/404; 367/305; 73/61.41; 73/61.42; 324/700

(58) Field of Classification Search
  USPC ......... 204/421–429, 404; 376/245; 367/305; 73/61.61, 61.42; 324/700
  See application file for complete search history.

(56) References Cited

U.S. PATENT DOCUMENTS

| | | | |
|---|---|---|---|
| 4,978,921 A | 12/1990 | Indig et al. | |
| 5,848,113 A | 12/1998 | Kim et al. | |
| 6,222,307 B1 * | 4/2001 | Roy et al. | 313/326 |
| 6,278,756 B1 * | 8/2001 | Jin Kim | 376/245 |
| 6,610,185 B2 | 8/2003 | Kim et al. | |
| 6,623,611 B1 * | 9/2003 | Jett et al. | 204/404 |
| 2002/0148558 A1 * | 10/2002 | Nieuwenhove | 156/273.7 |
| 2003/0132111 A1 * | 7/2003 | Kim et al. | 204/404 |

FOREIGN PATENT DOCUMENTS

| | | |
|---|---|---|
| JP | 3-17545 A | 1/1991 |
| JP | 11-142363 A | 5/1999 |
| JP | 11-148909 A | 6/1999 |
| JP | 2002-116281 A | 4/2002 |

(Continued)

OTHER PUBLICATIONS

R.L. Cowan et al., Experience with hydrogen water chemistry in boiling water reactors, Water Chemistry of Nuclear Reactor Systems 4, Bournemouth, U.K., Oct. 13-17, 1986, vol. 1, pp. 29-36.

(Continued)

*Primary Examiner* — J. Christopher Ball
*Assistant Examiner* — Jennifer Dieterle
(74) *Attorney, Agent, or Firm* — Mattingly & Malur, PC (57) ABSTRACT

An electrochemical corrosion potential sensor (ECP sensor) has an electrode cap, an electrode fixing body, a tubular insulator, a tubular metallic housing, and a conductive wire. Both ends of the tubular insulator are connected to the electrode fixing body and the tubular metallic housing respectively. A conductive wire passes through the tubular insulator and the tubular metallic housing, and is connected to an inner surface of the electrode fixing body. The electrode cap 11 disposed to cover an outer surface of the electrode fixing body. The ECP sensor with such a construction can lengthen the lifetime.

9 Claims, 4 Drawing Sheets

(56) References Cited

FOREIGN PATENT DOCUMENTS

| | | |
|---|---|---|
| JP | 2004-170421 A | 6/2004 |
| JP | 2005-140608 A | 6/2005 |
| JP | 4070322 B2 | 1/2008 |
| JP | 2009-42111 A | 2/2009 |

OTHER PUBLICATIONS

Tomonori Satoh et al., Atomic Energy Society of Japan, Autumn Conference 2005 at Hachinohe Institute of Technology, Sep. 13-15, 2005, p. 458.

Ronghua Zhang et al., Nanocrystalline ZrO2 thin films as electrode materials using in high temperature-pressure chemical sensors, Materials Letters 60, 2006, pp. 3170-3174.

Yoichi Wada et al., Hydrazine and Hydrogen Coinjection to Mitigate Stress Corrosion Cracking of Structural Materials in Boiling Water Reactors (VII)—Effects of Bulk Water Chemistry on ECP Distribution inside a Crack, Journal of Nuclear Science and Technology, vol. 44, No. 11, pp. 1448-1457, Nov. 2007.

Self-Sealing ECP Probe, GE Energy Technology Update, 2006.

\* cited by examiner

COMPRESSED PART

ELECTROCHEMICAL CORROSION POTENTIAL SENSOR

CLAIM OF PRIORITY

The present application claims priority from Japanese Patent application serial no. 2009-018947, filed on Jan. 30, 2009, the content of which is hereby incorporated by reference into this application.

BACKGROUND OF THE INVENTION

1. Technical Field

The present invention relates to electrochemical corrosion potential sensor, and particularly to an electrochemical corrosion potential sensor suitable for measuring an electrochemical corrosion potential of metallic member wetted by cooling water in a nuclear reactor during operation of a nuclear power plant.

2. Background Art

From the standpoint of improving operation rate of a nuclear power plant, critical problems include suppression of stress corrosion cracking and flow accelerated corrosion of structural materials (stainless steel and nickel base alloy) constituting reactor internals and pressure boundary components and materials (stainless steel, low-alloy steel, and carbon steel) constituting piping.

The stress corrosion cracking occurs when three factors, that is, material, stress, and corrosive environment meet specific conditions, and it can be mitigated by improving one of the three factors in the specific conditions. The flow accelerated corrosion also occurs when material and corrosive environment meet specific conditions, and it can be mitigated by improving one of the factors in the specific conditions.

Hydrogen water chemistry is one of the conventional technologies for improving the corrosive environment for the stress corrosion cracking. In a nuclear reactor, oxygen and hydrogen peroxide are generated due to radiolysis of the cooling water by neutrons and gamma rays. The cooling water containing oxygen and hydrogen peroxide forms a corrosive environment. The hydrogen water chemistry is the technology where feed water into which hydrogen has been injected is supplied into the nuclear reactor so that the hydrogen is reacted with the oxygen and hydrogen peroxide contained in the cooling water to reduce the concentration of the oxygen and hydrogen peroxide in the cooling water. The hydrogen water chemistry is the technology for improving the corrosive environment in the nuclear reactor. On the other hand, an oxygen injection is a technology for improving the corrosive environment concerning the flow accelerated corrosion. When the oxygen concentration in feed water decreases to 10 μg/L or less, the feed water pipe made of carbon steel is thinned down due to the flow accelerated corrosion by the feed water. The oxygen injection is the technology injecting oxygen into the feed water to suppress the flow accelerated corrosion of the feed water pipe.

The improvement effect of the corrosive environment improvement technologies is confirmed, for example, by measuring the electrochemical corrosion potential of targeted structural materials. For a boiling water reactor, the occurrence of the stress corrosion cracking is reported to be suppressed when the electrochemical corrosion potential is reduced to −0.23 V (SHE) or less (refer to R. L. Cowan, et al., "Experience with hydrogen water chemistry in boiling water reactors", Water Chemistry of Nuclear Reactor Systems 4, Bournemouth, U.K., Oct. 13-17, 1986, Vol. 1, p. 29 (1986)). Moreover, the occurrence of the flow accelerated corrosion is reported to be suppressed when the electrochemical corrosion potential is increased to −0.2 V (SHE) or more by the oxygen injection (refer to Tomonori Satoh, et al., Atomic Energy Society of Japan, Autumn Conference 2005 at Hachinohe Institute of Technology, Sep. 13-15, 2005, p. 458 (2005)). The potential expressed by V (SHE) means the potential relative to the standard hydrogen electrode.

The improvement effect of the corrosive environment improvement technologies is preferably confirmed by measuring the electrochemical corrosion potential throughout the operation cycles, because the flow condition of a plant may change during the operation of the nuclear power plant to vary the electrochemical corrosion potential. For that reason, the electrochemical corrosion potential is preferably measured for at least one operation cycle.

The electrochemical corrosion potential sensor (hereafter, referred to as ECP sensor) needs to generate a constant potential under use environment, and the electrode of the sensor needs to be electrically isolated from a measurement position. The corrosive potential is measured by an electro-meter as a potential difference between the measurement position and the ECP sensor. The ECP sensor used for measuring the corrosive potential is disclosed in for example, Japanese Patent Laid-open No. Hei 3(1991)-17545. The Japanese Patent Laid-open No. Hei 3(1991)-17545 describes the ECP sensor using platinum as its electrode. The ECP sensor generates the constant potential by generating a redox reaction of hydrogen on the surface of the platinum.

The ECP sensor has a structure in which the electrode and a metallic housing are electrically isolated by an insulator disposed between the electrode and the metallic housing. As the insulator, ceramics tolerable to the high-temperature environment and the radiation environment of the boiling water reactor are used. Connection between the electrode and the insulator and between the insulator and the metallic housing is performed by brazing after a surface of a connection section of the insulator is treated by placing thin metallic films on it (called metallization). Methods for suppressing the corrosion of the brazing parts are disclosed in Japanese Patent Laid-open No. Hei 11(1999)-148909 and Japanese Patent Laid-open No. 2002-116281. The Japanese Patent Laid-open No. Hei 11(1999)-148909 discloses a technology for suppressing the corrosion of the brazing part, in which a ceramics layer is placed on the brazing part to prevent the brazing part from directly coming in contact with high-temperature water. In addition, the Japanese Patent Laid-open No. 2002-116281 discloses a technology for suppressing the corrosion of the brazing part, in which platinum as a corrosion-resistant material is plated on the brazing part.

PRIOR ART LITERATURES

Patent Literatures

Patent Literature 1: Japanese Patent Laid-open No. Hei 3(1991)-17545
Patent Literature 2: Japanese Patent Laid-open No. Hei 11(1999)-148909
Patent Literature 3: Japanese Patent Laid-open No. 2002-116281

Non-Patent Literatures

Non-patent Literature 1: R. L. Cowan, et al., "Experience with hydrogen water chemistry in boiling water reactors", Water Chemistry of Nuclear Reactor Systems 4, Bournemouth, U.K., Oct. 13-17, 1986, Vol. 1, p. 29 (1986)

Non-patent Literature 2: Tomonori Satoh, et al., Atomic Energy Society of Japan, Autumn Conference 2005 at Hachinohe Institute of Technology, Sep. 13-15, 2005, p. 458

SUMMARY OF THE INVENTION

Problem for Solving by the Invention

A first problem is that a sensor having the electrode made of platinum is difficult to generate a constant potential in circumstances where the mole ratio of dissolved hydrogen to dissolved oxygen is less than 2. This is because, in addition to redox reaction of hydrogen on the platinum, redox reaction of oxygen on the platinum occurs, and overlap of each potential generated respectively by both reactions becomes unable to disregard. Since water quality changes according to operation condition of the nuclear power plant, it is preferable that the electrode of the ECP sensor is made of a metal that generates a constant potential regardless of the ratio of dissolved hydrogen to dissolved oxygen.

A second problem is that metal-ceramic joints of the insulator that connects and yet electrically insulates the electrode and the metallic housing break down easily. As described above, connection between the electrode and the insulator and between the insulator and the metallic housing is performed by brazing. In high-temperature water, there is a possibility that water penetrates into the ECP sensor to make the ECP sensor unfunctional in consequence of corrosion of the brazing part or separation of the metal-ceramic joints by stress due to thermal expansion differences between the electrode and the insulator or between the insulator and the metallic housing. Accordingly, so as to measure the electrochemical corrosion potential for a prolonged period by using the ECP sensor, critical problems to be solved are improving corrosion resistance of the brazing part and suppressing the separation of the metal-ceramic joints by stress due to the thermal expansion differences between the electrode and the insulator or between the insulator and the metallic housing. In particular, it becomes essential to examine countermeasures against the separation of the metal-ceramic joints by stress due to the thermal expansion differences between the electrode and the insulator or between the insulator and the metallic housing An object of the present invention is to provide an electrochemical corrosion potential sensor of which the lifetime can be further lengthened.

Means for Solving the Problem

A feature of the present invention for attaining the above object is an electrochemical corrosion potential sensor comprising a conductive electrode fixing body; an electrode cap member made of zirconium and fixed to the electrode fixing body; a tubular insulator connected to the electrode fixing body; a tubular metallic housing connected to the tubular insulator; and a conductive wire passing through the tubular insulator and the tubular metallic housing and connected to the electrode fixing body; wherein in a first connecting portion of the electrode fixing body and one end portion of the tubular insulator, the electrode fixing body is disposed outside of the tubular insulator and overlapped to the tubular insulator; in a second connecting portion of another end portion of the tubular insulator and the tubular metallic housing, the tubular metallic housing is disposed outside of the tubular insulator and overlapped to the tubular insulator; and the metallic cap member is disposed to cover an outer surface of the electrode fixing body.

The metallic cap made of zirconium that acts as the electrode and is disposed to cover the outer surface of the electrode fixing body is preferably disposed to cover an outer surface of a metal-ceramic joint of the electrode fixing body and the tubular insulator in addition to the outer surface of the electrode fixing body. As a consequence, corrosion of the metal-ceramic joint of the electrode fixing body and the tubular insulator can also be suppressed.

Moreover, if there is a clearance between the metallic cap and the tubular insulator, it is preferable to insert a metallic spacer made of zirconium into the clearance. By suppressing the diffusion of water to the outer surface, on which the metallic cap covers, of the metal-ceramic joint of the electrode fixing body and the tubular insulator, corrosion of the metal-ceramic joint of the electrode fixing body and the tubular insulator is also suppressed. In addition, separation of the metallic cap from the metal fixing body is further suppressed by fixing the metallic cap and the metallic spacer to each other by welding.

It is preferable to coat the outer surface of the metal-ceramic joint of the tubular insulator and the metallic housing with an interlayer, and, additionally, coat an outer surface of the interlayer with platinum in addition to coating of the outer surface of the electrode fixing body and the outer surface of the metal-ceramic joint of the electrode fixing body and the tubular insulator. The structure described above is more preferable because the corrosion of both the metal-ceramic joints of the electrode fixing body and the tubular insulator, and the tubular insulator and the metallic housing can be suppressed.

Advantageous Effect of the Invention

According to the present invention, the lifetime of the electrochemical corrosion potential sensor can be further lengthened.

DETAILED DESCRIPTION OF THE PREFERRED EMBODIMENTS

Embodiments of the present invention are described below with reference to the drawings.

Embodiment 1

Figure 1:
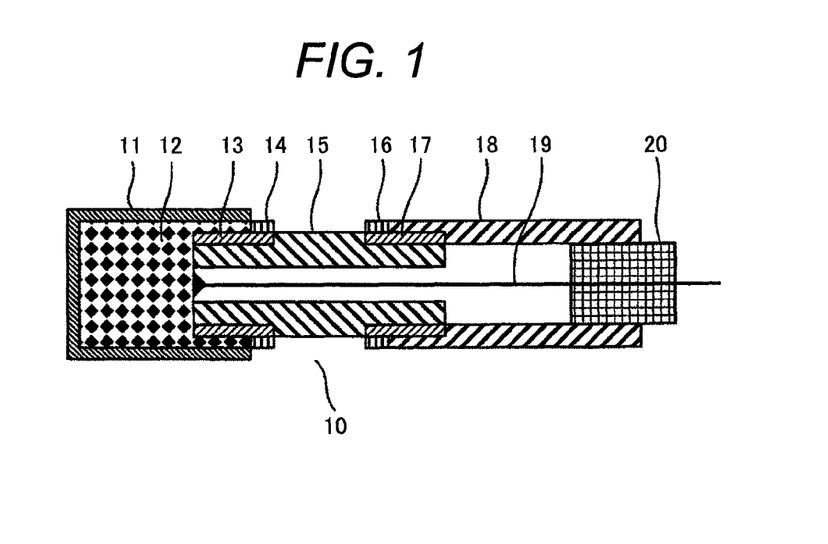
FIG. 1 is a longitudinal section view showing an electrochemical corrosion potential sensor according to embodiment 1 which is a preferred embodiment of the present invention.
Figure 2:
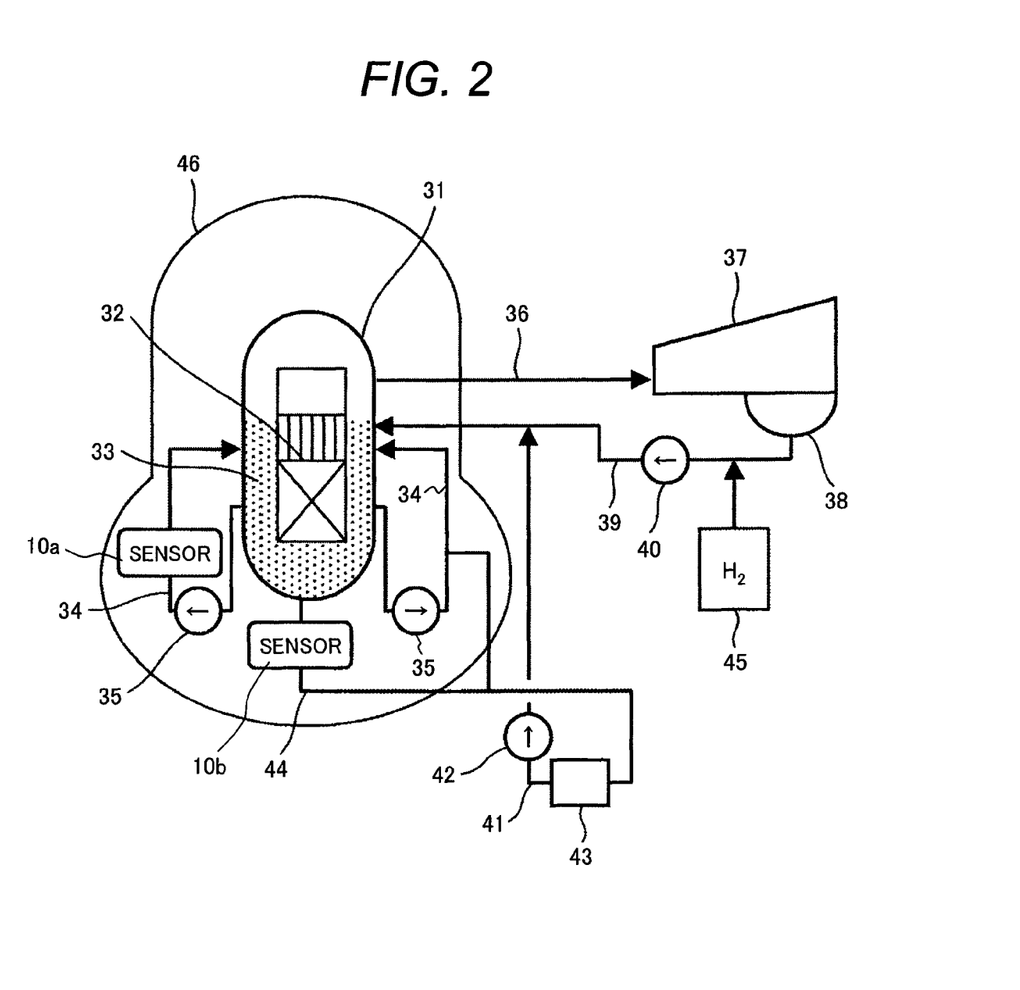
FIG. 2 is a detailed structural diagram showing a BWR plant to which the electrochemical corrosion potential sensor shown in FIG. 1 is installed.
Figure 3:
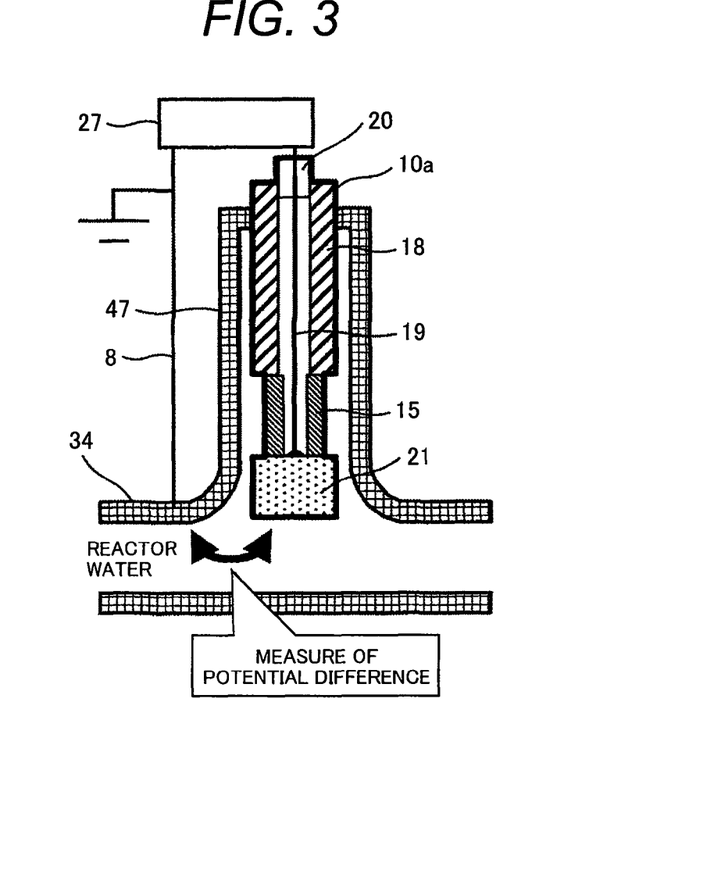
FIG. 3 is a detailed structural diagram showing the installation status of the electrochemical corrosion potential sensor shown in FIG. 1 to a primary loop recirculation piping shown in FIG. 2.

An electrochemical corrosion potential sensor (ECP sensor) according to embodiment 1 which is a preferred embodiment of the present invention is described with reference to FIGS. 1 to 3. The ECP sensor 10 of the present embodiment is applied to, for example, a boiling water reactor plant (BWR plant). First, general construction of the BWR plant to which the ECP sensor 10 is applied is described with reference to FIG. 2.

The BWR plant is provided with a nuclear reactor, a feed water system, a primary loop recirculation system, a main steam system, a turbine 37, a condenser 38, and a reactor water clean-up system. The nuclear reactor 30 has a reactor pressure vessel 31 (referred to as RPV), and a core 32 is disposed in the RPV 31. A plurality of fuel assemblies (not shown) are loaded in the core 32. The feed water system has feed water pipe 39 that connects the condenser 38 and the RPV 31. The feed water pump 40 is placed in the feed water pipe 39. The main steam system has main steam pipe 36 that connects the RPV 31 and the turbine 37. The primary loop recirculation system has a recirculation pipe 34 connected to the RPV 31 and a recirculation pump 35 placed in the recirculation pipe 34. The RPV 31 and the primary loop recirculation system are disposed in a reactor containment vessel 46. The reactor water clean-up system has clean-up system pipe 41 connected to the recirculation pipe 34 and the feed water pipe 39 and a clean-up system pump 42 and a clean-up apparatus 43 disposed in clean-up system pipe 41. A hydrogen supply apparatus 45 is connected to the feed water pipe 39.

Cooling water (reactor water) in the RPV 31 is heated by heat generated by nuclear fission of nuclear fuel material contained in the fuel assemblies loaded in the core 32, and a part of the cooling water is vaporized. The steam generated by vaporizing is exhausted from the RPV 31 and is supplied to the turbine 37 through the main steam pipe 36, and rotates the turbine 37. A generator coupled to the turbine 37 is rotated, and generates electric power. The steam exhausted from the turbine 37 is condensed at a condenser 38 to be water. The condensate, that is, the feed water is pressurized by the feed water pump 40 and is supplied into the RPV 31 through the feed water pipe 39. Hydrogen is injected from the hydrogen supply apparatus 45 into the feed water flowing in the feed water pipe 39, and is introduced to the RPV 31 along with the fed water. The reactor water contains the hydrogen.

Most of the reactor water, which was not vaporized, is separated from steam by a steam separator (not shown) disposed in the RPV 31. The separated reactor water descends in a downcomer 33 formed between the RPV 31 and the core 32, and flows into the recirculation pipe 34. The recirculation pump 35 pressurizes the reactor water. The pressurized reactor water is ejected from a nozzle (not shown) of a jet pump (not shown) disposed in the downcomer 33 into a bell mouth (not shown) of the jet pump, and sucks reactor water around the nozzle in the downcomer 33 into the bell mouth. The reactor water discharged from the jet pump is supplied into the core 32. The feed water containing hydrogen introduced through the feed water pipe 39 is mixed with the reactor water separated by the steam separator, in the downcomer 33. A part of the reactor water flowed into the recirculation pipe 34 is introduced into the clean-up system piping 41, and is cleaned up by the clean-up apparatus 43 disposed in the clean-up system pipe 41. The reactor water exhausted from the clean-up apparatus 43 is returned into the RPV 31 through the clean-up system pipe 41 and the feed water pipe 39. A bottom drain pipe 44 connected to the bottom of the RPV 31 is connected to the clean-up system pipe 41.

ECP sensors 10 (see FIG. 1) are disposed in the recirculation pipe 34 and the bottom drain pipe 44 respectively. The ECP sensor 10 disposed in the recirculation pipe 34 is referred to as ECP sensor 10a, and the ECP sensor 10 disposed in the bottom drain pipe 44 is referred to as ECP sensor 10b. Each of the ECP sensors 10a and 10b has a construction of the ECP sensor 10 described below.

Concrete construction of the ECP sensor 10 of the present embodiment is described below with reference to FIG. 1. The ECP sensor 10 has an electrode cap 11, an electrode fixing body 12, a tubular insulator 15, a tubular metallic housing 18, and a conductive wire 19. The electrode cap 11 is made of metallic zirconium. The tubular insulator 15 is made of sapphire. Alternatively, the tubular insulator 15 may be made of stabilized zirconia. The tubular metallic housing 18 is made of Fe-29Ni-17Co alloy. The tubular metallic housing 18 may be made of Fe-42Ni alloy or Fe-36Ni alloy besides Fe-29Ni-17Co alloy. Both ends of the tubular insulator 15 are respectively connected to the electrode fixing body 12 and the tubular metallic housing 18. A metalized metallization section 13 is formed on one end of the tubular insulator 15, which is connected to the electrode fixing body 12. Also a metalized metallization section 17 is formed on the other end of the tubular insulator 15, which is connected to the tubular metallic housing 18. The electrode fixing body 12 that is formed to be a cap-like shape by blocking off of one end is united to the tubular insulator 15 by brazing with an inner surface of the electrode fixing body 12 being in contact with the metallization part 13. Reference number 14 is the brazing part of the electrode fixing body 12 and the tubular insulator 15. The tubular metallic housing 18 is united to the tubular insulator 15 by brazing with an inner surface of the tubular metallic housing 18 being in contact with the metallization part 17. Reference number 16 is the brazing part of the tubular metallic housing 18 and the tubular insulator 15. The conductive wire 19 passes through the tubular insulator 15 and the tubular metallic housing 18, and is connected to the inner surface of the electrode fixing body 12. A conductive wire drawing jig 20 that constitutes a blocking off part is fixed in the other end of the tubular metallic housing 18 to block off the tubular metallic housing 18. The conductive wire 19 is made to penetrate the conductive wire drawing jig 20 and is taken out from the tubular metallic housing 18, that is, the ECP sensor 10.

A MI (mineral insulated) cable is used as the conductive wire drawing jig 20. If the joint of the tubular metallic housing 18 with the tubular insulator 15 is made of Fe-29Ni-17Co alloy, Fe-42Ni alloy, or Fe-36Ni, the rest of the tubular metallic housing 18 may be made of stainless steel. In this case, the tubular metallic housing 18 is composed of stainless steel united to one of Fe-29Ni-17Co alloy, Fe-42Ni alloy, or Fe-36Ni alloy. Tungsten, titanium, or molybdenum-manganese is used for the metallization of the both ends of the tubular insulator 15.

Figure 4:
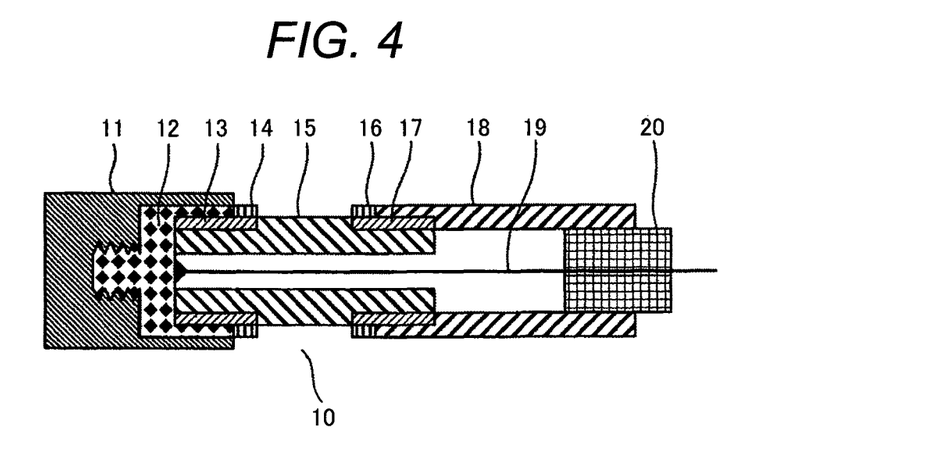
FIG. 4 is a longitudinal section view showing the electrochemical corrosion potential sensor shown in FIG. 1 in which the electrode cap is provided with internal threads and the electrode fixing body is provided with external threads.

The electrode cap 11 is disposed so that it covers the electrode fixing body 12. As shown in FIG. 4, it is preferable to provide the electrode fixing body 12 with an internal thread and the electrode cap 11 with an external thread, or the electrode fixing body 12 with an external thread and the electrode cap 11 with an internal thread to fix them with threads because the electrode cap 11 becomes difficult to remove from the electrode fixing body 12.

According to the structure described above, a function to be connected to the tubular insulator 15 and prevent water from coming into the ECP sensor and a function to generate a constant potential are performed by different members, and accordingly a longer lifetime of the ECP sensor can be realized.

Attachment structure of the ECP sensor 10 to the BWR plant is described with reference to FIG. 3. Since the ECP sensor 10a and 10b have the same attachment structure, the attachment structure of the ECP sensor 10a is used for explanation. An attachment pipe 47 to which the ECP sensor 10a is attached is fixed to the recirculation pipe 34 at a targeted measurement point like a branch pipe. The ECP sensor 10a is inserted into the attachment pipe 47 and attached to the attachment pipe 47 so that an electrode 21 (with the present embodiment, the electrode fixing body 12 covered with the electrode cap 11) faces toward the central axis of the circulation pipe 34. A clearance between an end portion of the attachment pipe 47 and the ECP sensor 10a is sealed with a sealing member so as to prevent the reactor water flowing in the circulation pipe 34 from leaking. The conductive wire 19 reaches outside of the attachment pipe 47 and is connected to an electro-meter 27. The other lead wire connected to the electro-meter 27 is connected to the circulation pipe 34. The electrode 21 and the circulation pipe 34 are not electrically contacted. The ECP sensor 10b is attached to the attachment pipe 47 (not shown) disposed in the bottom drain pipe 44 in a similar way as the ECP sensor 10a.

The ECP sensor 10a detects a potential difference generated between the electrode 21 and the recirculation pipe 34. The potential difference is measured by the electro-meter 27, and the electrochemical corrosion potential of the recirculation pipe 34 near the electrode 21 is obtained on the basis of the potential difference measured by the electro-meter 27.

Since zirconium is corroded to zirconium oxide by oxygen or water, thereby generating potential, zirconium is not affected by hydrogen. For that reason, according to the ECP sensor 10 of the present embodiment, a constant potential can be generated regardless of dissolved hydrogen relative to dissolved oxygen. At the same time, when using zirconium as the electrode, if zirconium is contacted with a different metal and brought into contact with water, potential generated by the different metal may exerts an effect. When zirconium corrodes to form a zirconium oxide film on it, the corrosion is suppressed. When zirconium is united to a metal having a large corrosion rate, potential caused by the metal having a large corrosion rate exerts an effect. Consequently, bringing the electrode fixing body 12 into contact with water needs to be suppressed.

The electrode fixing body 12 has a function to be connected to the tubular insulator 15 and prevent water from coming into the ECP sensor 10 and a function to electrically connect the electrode cap 11 acted as the electrode to the electrode fixing body 12 and the electrode fixing body 12 to the conductive wire 19. In other words, the function to be connected to the tubular insulator 15 and prevent water from coming into the ECP sensor 10 and the function to generate a constant potential are performed by different members. In the conventional technology, the electrode is directly connected to the tubular insulator, and performs the function to prevent water from coming into the ECP sensor and the function to generate a constant potential. On that point, the present embodiment is different from the conventional technology. By this means, suitable material for the electrode fixing body 12 can be used to suppress separation of the metal-ceramic joints by stress due to thermal expansion differences between the electrode fixing body 12 and the tubular insulator 15.

Figure 5:
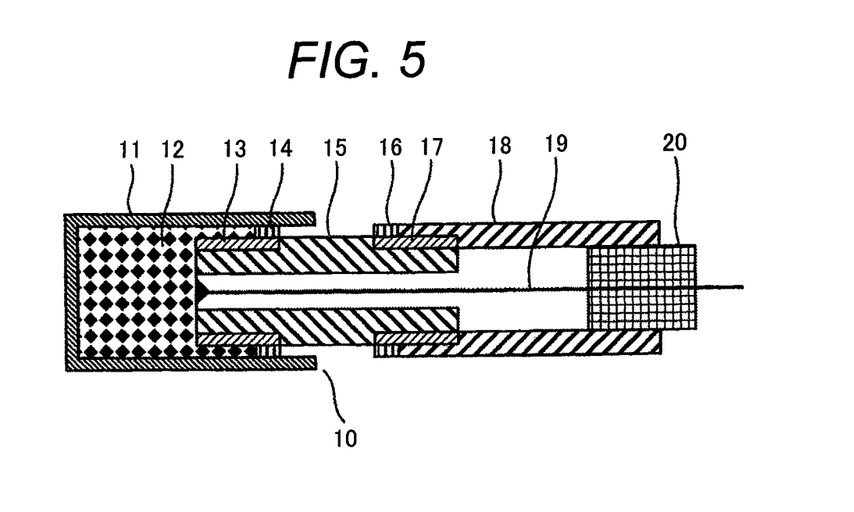
FIG. 5 is a longitudinal section view showing an electrochemical corrosion potential sensor of a modification to embodiment 1.

As a modification of embodiment 1, as shown in FIG. 5, the electrode cap 11 is formed to cover the brazing part 14, that is, the metal-ceramic joint of the electrode fixing body 12 and the tubular insulator 15, while the electrode cap 11 is formed to cover only the outer surface of the electrode fixing body 12 in the embodiment 1. The modification is suitable for lengthening the lifetime of the ECP sensor 10, because water being brought in contact with the brazing part 14 causes stagnancy by covering the brazing part 14 and the dissolved oxygen in the water is lowered, thereby suppressing the corrosion of the brazing part 14.

Figure 6:
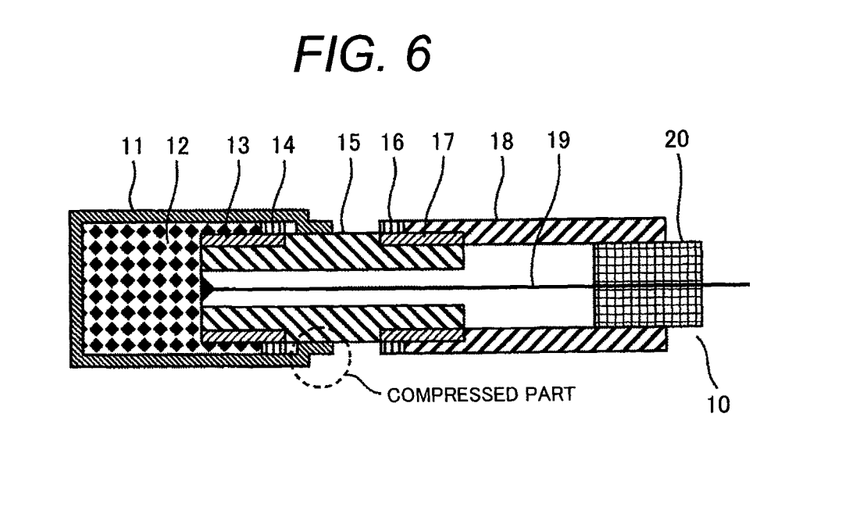
FIG. 6 is a longitudinal section view showing an electrochemical corrosion potential sensor of another modification to embodiment 1.

Moreover, as shown in FIG. 6, it is suitable for lengthening the lifetime of the ECP sensor 10 to mechanically compress an opening portion of the electrode cap 11 so that the opening portion contact with the tubular insulator 15, because contact of water to the brazing part 14 is suppressed and the corrosion of the brazing part 14 is suppressed. In addition, it is also suitable for anti-falling of the electrode cap 11 to mechanically compress the opening portion of the electrode cap 11 so that the opening portion is in contact with the tubular insulator 15.

Figure 7:
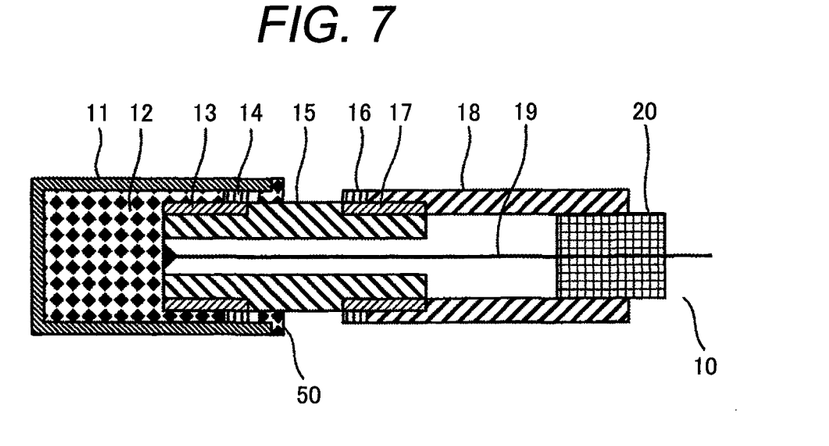
FIG. 7 is a longitudinal section view of an ECP sensor of another modification to embodiment 1.

As another modification of embodiment 1, as shown in FIG. 7, the electrode cap 11 is formed to cover the brazing part 14, that is, the metal-ceramic joint of the electrode fixing body 12 and the tubular insulator 15, while the electrode cap 11 is formed to cover only the outer surface of the electrode fixing body 12 in embodiment 1. A metallic spacer 50 made of the same metal as the electrode cap 11 is further inserted into the clearance between the electrode cap 11 and the tubular insulator 15. The modification is suitable for lengthening the lifetime of the ECP sensor 10, because the modification makes it hard for water to penetrate into the brazing part 14, thereby suppressing the corrosion of the brazing part 14. In addition, it is suitable for anti-falling of the electrode cap 11 to fix the electrode cap 11 and the metallic spacer 50 to each other by welding.

Embodiment 2

Figure 8:
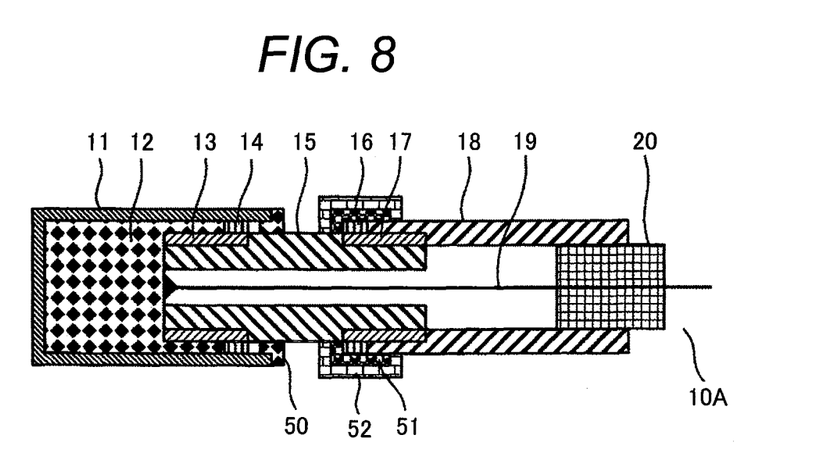
FIG. 8 is a longitudinal section view showing an electrochemical corrosion potential sensor according to embodiment 2 which is another embodiment of the present invention.

An ECP sensor according to embodiment 2 which is another embodiment of the present invention is described with reference to FIG. 8. (the embodiment 1 shown in FIG. 7 is applied as a representation.) The ECP sensor 10A of the present embodiment has a structure in which an interlayer 51 is disposed on an outer surface of a brazing part 16, and an outer surface of the interlayer 51 is coated with a platinum layer 52 in addition to the ECP sensor 10 of the embodiment 1. Titanium is suitable for the interlayer 51 if Fe-29Ni-17Co alloy or Fe-42Ni alloy is used for the electrode fixing body 12. The interlayer 51 and the platinum layer 52 as a coating layer can be formed, for example, by chemical vapor deposition (CVD), ion-plating or ion-sputtering. A thickness of 0.5-1.0 µm is enough for the coating layer.

According to the ECP sensor 10A of the present embodiment, the same effect as that of embodiment 1 can be acquired.

According to the ECP sensor 10A of the present embodiment, the lifetime of the ECP sensor 10A can be further lengthened, because the corrosion of the metal-ceramics joint of the tubular insulator 15 and the tubular metallic housing 18 can be suppressed, and water is prevented from entering into the tubular metallic housing 18 from the joint.

The ECP sensors of the embodiments 1 and 2 can be applied to a pressurized water reactor (PWR), a thermal power plant, and a chemical plant.

REFERENCE SIGNS LIST 10, 10a, 10b: electrochemical corrosion potential sensor, 11: electrode cap, 12: electrode fixing body, 13, 17: metallization section, 14: brazing part, 15: tubular insulator, 18: tubular metallic housing, 19: conductive wire, 20: conductive wire drawing jig, 21: electrode, 31: reactor pressure vessel, 32: core, 33: downcomer, 34: recirculation pipe, 35: recirculation pump, 36: main steam pipe, 37: turbine, 38: condenser, 39: feed water pipe, 40: feed water pump, 41: clean-up system pipe, 42: clean-up system pump, 43: clean-up apparatus, 44: bottom drain pipe, 45: hydrogen supply apparatus, 46: reactor containment vessel, 50: metallic spacer, 51: interlayer, 52: platinum layer.

What is claimed is:

1. An electrochemical corrosion potential sensor comprising:
    a conductive electrode fixing body;
    an electrode cap member made of zirconium and fixed to the electrode fixing body;
    a tubular insulator connected to the electrode fixing body;
    a tubular metallic housing connected to the tubular insulator; and
    a conductive wire passing through the tubular insulator and the tubular metallic housing and connected to the electrode fixing body;
    wherein in a first connecting portion of the electrode fixing body and one end portion of the tubular insulator, the electrode fixing body is disposed outside of the tubular insulator and overlapped to the tubular insulator;
    wherein in a second connecting portion of another end portion of the tubular insulator and the tubular metallic housing, the tubular metallic housing is disposed outside of the tubular insulator and overlapped to the tubular insulator;
    wherein the electrode cap member is disposed to cover an outer surface of the electrode fixing body;
    wherein the electrode cap member is disposed to cover the outer surface of the electrode fixing body and an outer surface of the first connecting portion; and
    wherein a metallic spacer made of zirconium is disposed in a clearance between the electrode cap member and the tubular insulator.

2. The electrochemical corrosion potential sensor according to claim 1, wherein the electrode cap member and the metallic spacer are fixed to each other by welding.

3. The electrochemical corrosion potential sensor according to claim 1, wherein an outer surface of the second connecting portion is covered with an interlayer; and a surface of the interlayer is covered with platinum.

4. The electrochemical corrosion potential sensor according to claim 3, wherein the interlayer is composed of titanium.

5. The electrochemical corrosion potential sensor according to claim 1, wherein a coefficient of linear expansion of each of the electrode fixing body and the tubular metallic housing is smaller than a coefficient of linear expansion of the tubular insulator.

6. The electrochemical corrosion potential sensor according to claim 5, wherein the electrode fixing body and the tubular metallic housing are made of Fe-29Ni-17Co alloy or Fe-42Ni alloy.

7. The electrochemical corrosion potential sensor according to claim 5, wherein the tubular insulator is sapphire or stabilized zirconia.

8. The electrochemical corrosion potential sensor according to claim 1, wherein a first metallization section is formed on an outer surface of the tubular insulator in the first connecting portion, and the first metallization section is connected with the electrode fixing body by metal.

9. The electrochemical corrosion potential sensor according to claim 1, wherein a second metallization section is formed on an outer surface of the tubular insulator in the second connecting portion, and the second metallization section is connected with the tubular metallic housing by metal.

* * * * *